US009456796B2

United States Patent
Han et al.

(10) Patent No.: US 9,456,796 B2
(45) Date of Patent: Oct. 4, 2016

(54) X-RAY IMAGING APPARATUS AND METHOD OF CONTROLLING THE SAME

(71) Applicants: SAMSUNG ELECTRONICS CO., LTD., Suwon-si (KR); SAMSUNG LIFE PUBLIC WELFARE FOUNDATION., Seoul (KR)

(72) Inventors: Seok Min Han, Seongnam-si (KR); Dong Goo Kang, Hwaseong-si (KR); Sung Hoon Kang, Suwon-si (KR); Young Hun Sung, Hwaseong-si (KR); Myung Jin Chung, Seoul (KR)

(73) Assignees: SAMSUNG ELECTRONICS CO., LTD., Suwon-si (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 244 days.

(21) Appl. No.: 14/452,643

(22) Filed: Aug. 6, 2014

(65) Prior Publication Data
US 2015/0063528 A1 Mar. 5, 2015

(30) Foreign Application Priority Data
Aug. 30, 2013 (KR) .......................... 10-2013-0103947

(51) Int. Cl.
*H05G 1/64* (2006.01)
*A61B 6/00* (2006.01)

(52) U.S. Cl.
CPC ............ *A61B 6/482* (2013.01); *A61B 6/405* (2013.01); *A61B 6/5235* (2013.01); *A61B 6/583* (2013.01); *A61B 6/487* (2013.01); *A61B 6/502* (2013.01); *A61B 6/504* (2013.01)

(58) Field of Classification Search
CPC ........ A61B 6/482; A61B 6/032; A61B 6/502; A61B 6/5205
USPC ................ 378/4–20, 37, 54, 62, 98.11, 98.12
See application file for complete search history.

(56) References Cited

U.S. PATENT DOCUMENTS

| 6,683,934 B1* | 1/2004 | Zhao ...................... A61B 6/032 |
| | | 378/37 |
| 2009/0135994 A1 | 5/2009 | Yu et al. |
| 2012/0224668 A1 | 9/2012 | Baetz et al. |

FOREIGN PATENT DOCUMENTS

| JP | 2005-6918 A | 1/2005 |
| JP | 2009-195471 A | 9/2009 |
| JP | 2010-75555 A | 4/2010 |
| JP | 2010-246958 A | 11/2010 |
| KR | 10-2012-0041557 A | 5/2012 |
| KR | 10-2014-0043520 A | 4/2014 |

* cited by examiner

*Primary Examiner* — Courtney Thomas
(74) *Attorney, Agent, or Firm* — Sughrue Mion, PLLC

(57) ABSTRACT

Disclosed herein are an X-ray imaging apparatus and a method for controlling the same. The X-ray imaging apparatus includes an X-ray generator configured to radiate first-energy X-rays toward an object, an X-ray detector configured to detect the first-energy X-rays which propagate through the object, an image processor configured to generate a first object image which correspond to the detected first-energy X-rays and to estimate a second object image which corresponds to second-energy X-rays based on the generated first object image, and a controller configured to control the image processor to repeatedly estimate the second object image by controlling the X-ray generator to repeatedly radiate the first-energy X-rays toward the object.

18 Claims, 16 Drawing Sheets

X-RAY IMAGING APPARATUS AND METHOD OF CONTROLLING THE SAME

CROSS-REFERENCE TO RELATED APPLICATION

This application claims priority from Korean Patent Application No. 10-2013-0103947, filed on Aug. 30, 2013 in the Korean Intellectual Property Office, the disclosure of which is incorporated herein by reference in its entirety.

BACKGROUND

1. Field

Exemplary embodiments relate to an X-ray imaging apparatus for generating an X-ray image by radiating X-rays to an object, and a method of controlling the same.

2. Description of the Related Art

An X-ray imaging apparatus is an apparatus which is capable of obtaining an image of inside an object by radiating X-rays toward the object and detecting the X-rays which propagate through the object. Since X-ray transmission varies based on characteristics of a material inside the object, the internal structure of the object may be imaged by detecting the intensity of X-rays which propagate through the object.

Conventionally, an X-ray image was typically obtained by radiating X-rays having a single energy level. In this case, drawing a distinction between a calcified nodule and a non-calcified nodule, or between a nodule and a mass of microtissues, may be difficult.

As such, currently, a technique of separating materials inside an object based on a plurality of X-ray images which correspond to different energy levels has been developed and is being researched in various ways.

A scheme of obtaining a plurality of X-ray images which correspond to different energy levels includes a scheme of separately radiating X-rays having different energy bands, and a scheme of radiating X-rays having different energy bands once and then separating detected X-rays according to energy bands.

SUMMARY

Therefore, it is an aspect of one or more exemplary embodiments to provide an X-ray imaging apparatus which is capable of estimating a multi-energy image using thickness information of an object and a single-energy image, and repeatedly performing the estimation operation in the time domain, and a method of controlling the same.

Additional aspects of the exemplary embodiments will be set forth in part in the description which follows and, in part, will be obvious from the description, or may be learned by practice of the exemplary embodiments.

In accordance with one aspect of one or more exemplary embodiments, an X-ray imaging apparatus includes an X-ray generator configured to radiate first-energy X-rays toward an object, an X-ray detector configured to detect the first-energy X-rays which propagate through the object, an image processor configured to generate a first object image which corresponds to the detected first-energy X-rays and to estimate a second object image which corresponds to second-energy X-rays based on the generated first object image, and a controller configured to control the image processor to repeatedly estimate the second object image by controlling the X-ray generator to repeatedly radiate the first-energy X-rays toward the object.

In accordance with another aspect of one or more exemplary embodiments, a method for controlling an X-ray imaging apparatus includes an X-ray radiating operation to radiate first-energy X-rays toward an object, an X-ray detecting operation to detect the first-energy X-rays which propagate through the object, an image processing operation to generate a first object image which corresponds to the detected first-energy X-rays and to estimate a second object image which corresponds to second-energy X-rays based on the generated first object image, and a controlling operation to control the second object image to be repeatedly estimated by repeatedly radiating the first-energy X-rays toward the object.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
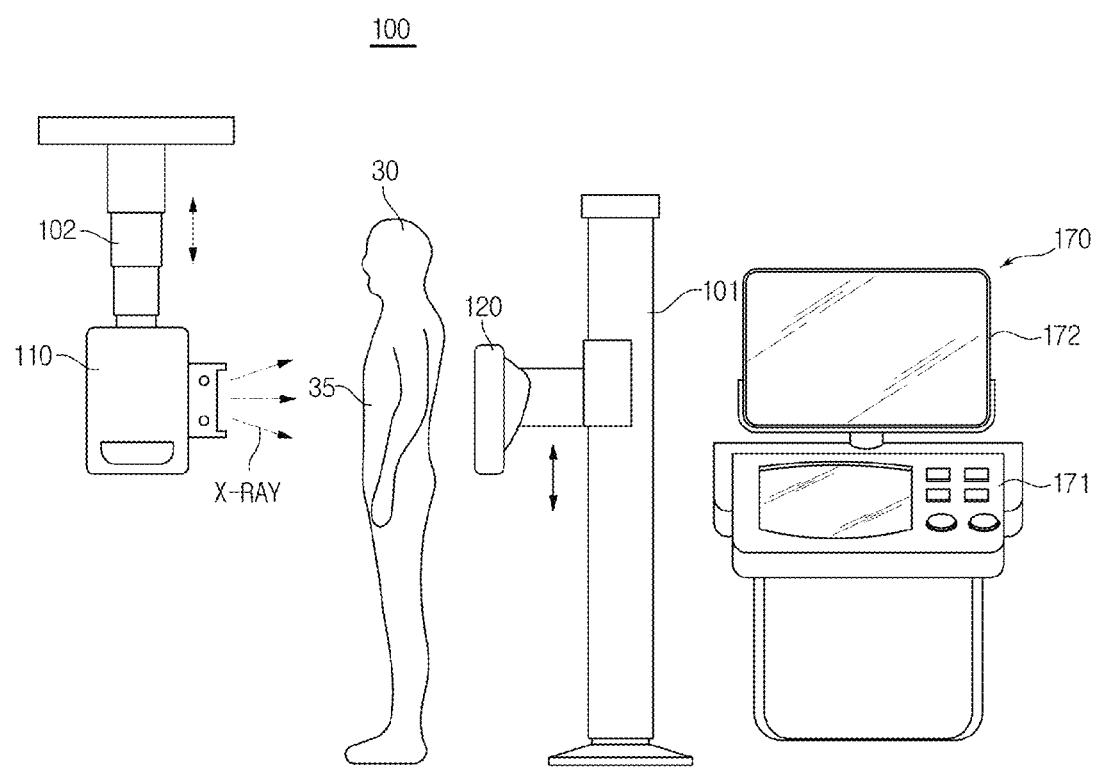
FIG. 1 is an external view of a general X-ray imaging apparatus.

Reference will now be made in detail to exemplary embodiments, examples of which are illustrated in the accompanying drawings, wherein like reference numerals refer to like elements throughout.

An X-ray imaging apparatus may have a different structure or imaging scheme depending on a part to be imaged, a type of an X-ray image, and/or a purpose of imaging. Specifically, there are a general X-ray imaging apparatus configured to image the chest, arms, legs, and/or any other suitable body part, an X-ray imaging apparatus which uses mammography to image the breast, an X-ray imaging apparatus which uses fluoroscopy, an X-ray imaging apparatus which uses angiography, an X-ray imaging apparatus for cardiography, an X-ray imaging apparatus which uses tomography, etc. An X-ray imaging apparatus according to an exemplary embodiment may be one or a combination of the above-mentioned X-ray imaging apparatuses.

FIG. 1 is an external view of a general X-ray imaging apparatus 100.

Referring to FIG. 1, the general X-ray imaging apparatus 100 may include an X-ray generator 110, an X-ray detector 120, and a host device 170.

The X-ray generator 110 may generate X-rays to obtain an X-ray image of an object 35 and may radiate the generated X-rays toward a subject 30.

Here, the subject 30 may be, but is not limited to, a living body of a person or an animal, and may include any entity for which an internal structure may be imaged by using the X-ray imaging apparatus 100.

The object 35 refers to an internal part of the subject 30 to be diagnosed by using the X-ray imaging apparatus 100, i.e., a part to be radiographed. Therefore, in the case of the general X-ray imaging apparatus 100 illustrated in FIG. 1, the object 35 may be any one or more of the chest, arms, legs, and/or any other suitable body part.

The X-ray generator 110 may be connected to a ceiling via a holder 102 mounted on the X-ray generator 110. The holder 102 may have a length which is adjustable in a vertical direction, and thus the position of the X-ray generator 110 may be adjusted to correspond to the position of the object 35 by adjusting the length of the holder 102.

The X-ray detector 120 may be disposed to face the X-ray generator 110 with respect to the object 35 and may detect the X-rays radiated from the X-ray generator 110 and which propagate through the object 35. In addition, the X-ray detector 120 may convert the detected X-rays into an electrical signal.

One end of the X-ray detector 120 may be mounted on a support fixture 101 movably in a vertical direction. Thus, the position of the X-ray detector 120 may be adjusted to correspond to the position of the object 35.

Unlike FIG. 1, the subject 30 may lie on a table, the X-ray generator 110 may be mounted on the ceiling movably in a length direction of the table, and the X-ray detector 120 may be mounted in the table movably in the length direction of the table.

The host device 170 may include an input unit (also referred to herein as an "input device") 171 configured to receive a command from a user, and a display unit (also referred to herein as a "display device" and/or as a "display") 172 configured to display an X-ray image, and thus may provide a user interface. Here, the user may be, but is not limited to, a person who diagnoses the object 35 by using the X-ray imaging apparatus 100, such as for example, a doctor, radiologist, or nurse, and may include any one who uses the X-ray imaging apparatus 100.

The input unit 171 may include, but is not limited to, at least one of a switch, a keyboard, a track ball, and a touchscreen.

The display unit 172 may be, but is not limited to, a cathode ray tube (CRT), a liquid crystal display (LCD) device, an organic light-emitting diode (OLED), and/or any other suitable type of display device.

Figure 2:
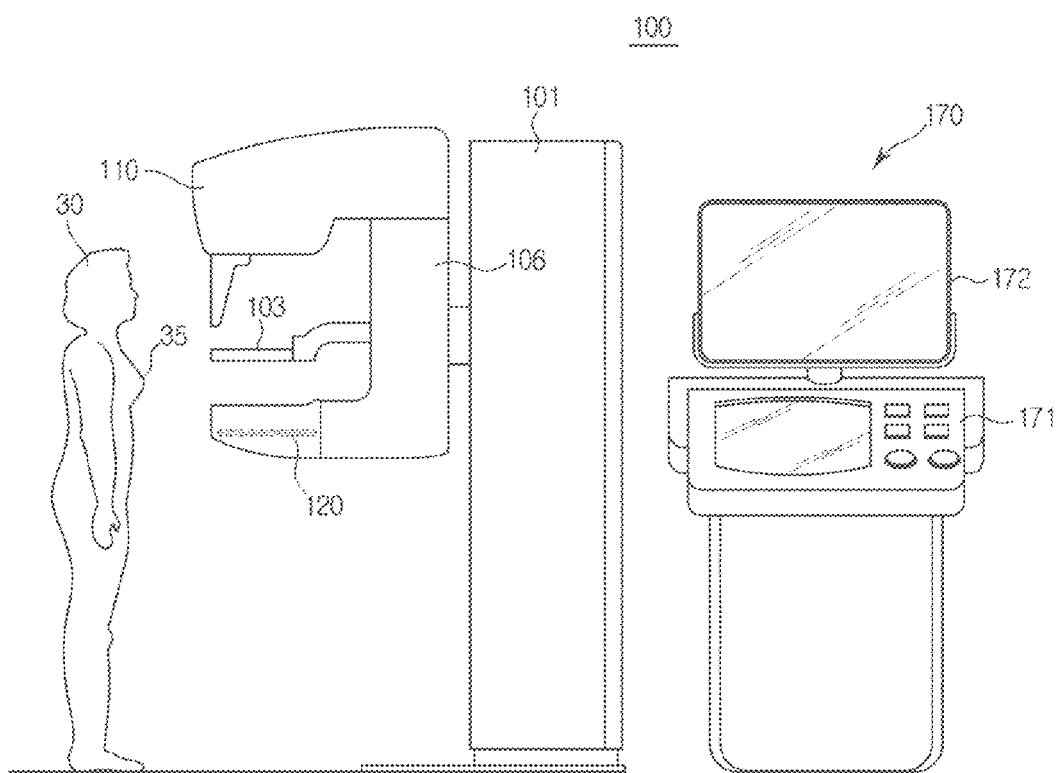
FIG. 2 is an external view of an X-ray imaging apparatus configured to image the breast.

FIG. 2 is an external view of an X-ray imaging apparatus 100 configured to image the breast.

Referring to FIG. 2, like FIG. 1, the X-ray imaging apparatus 100 may include the X-ray generator 110, the X-ray detector 120, and the host device 170.

However, unlike FIG. 1, the X-ray imaging apparatus 100 may dispose the X-ray generator 110 and the X-ray detector 120 respectively above and below the object 35 and may radiate X-rays from above the object 35.

In addition, the X-ray imaging apparatus 100 may further include compression paddles 103 which are disposed between the X-ray generator 110 and the X-ray detector 120 and configured to compress the object 35. Here, the object 35 is the breast and a high-contrast X-ray image of the object 35 may be achieved by compressing the object 35 using the compression paddles 103.

The compression paddles 103 may be mounted on a frame 106 movably in a vertical direction and may move to adjust a level of compression.

The X-ray generator 110 and the X-ray detector 120 may be connected via the frame 106 which may be mounted on the support fixture 101 in such a manner that the height of the frame 106 is adjustable in a vertical direction. Thus, the object 35 may be disposed between the X-ray generator 110 and the X-ray detector 120, and more particularly, on the compression paddles 103 between the X-ray generator 110 and the X-ray detector 120, by adjusting the height of the frame 106.

The X-ray generator 110 of the X-ray imaging apparatus 100 will now be described in detail with reference to FIGS. 3, 4, and 5.

The X-ray generator 110 includes an X-ray tube 111 configured to generate X-rays.

Figure 3:
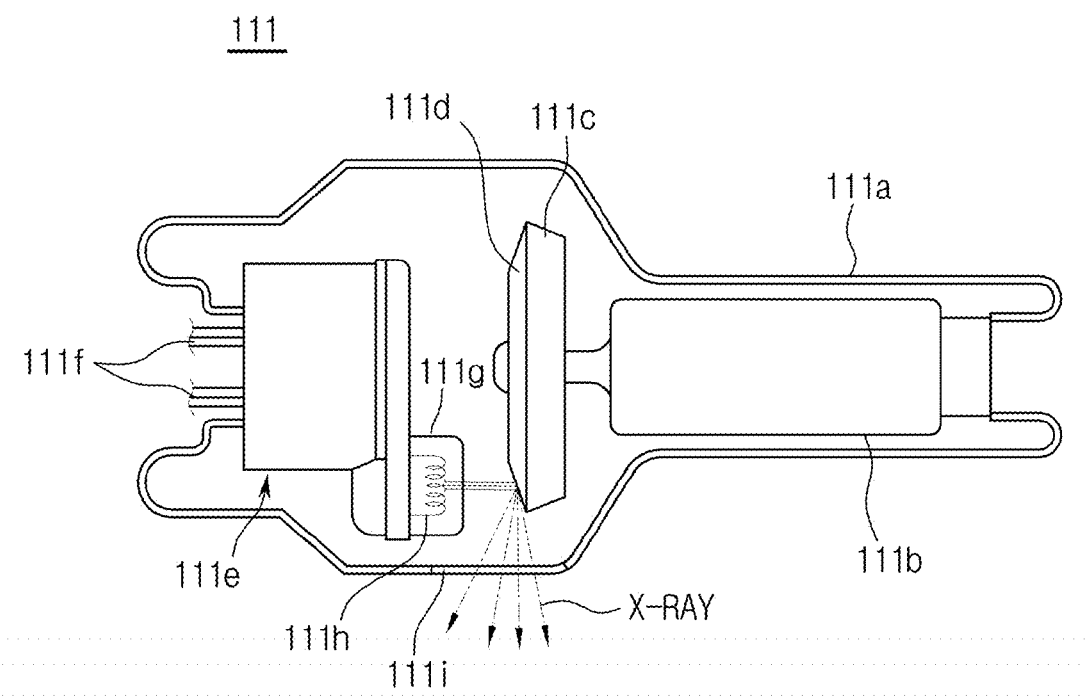
FIG. 3 is a view illustrating the configuration of an X-ray tube.

FIG. 3 is a view illustrating the configuration of the X-ray tube 111.

Referring to FIG. 3, the X-ray tube 111 may be formed as a diode which includes an anode 111c and a cathode 111e, and may use a glass tube 111a formed of hard silica glass or the like.

The cathode 111e includes a filament 111h and a focusing electrode 111g to focus electrons, and the focusing electrode 111g is also referred to as a focusing cup. The glass tube 111a is evacuated to a high-vacuum state of about 10 mm Hg, and the filament 111h of the cathode 111e is heated at high temperature to generate thermoelectrons. An example of the filament 111h is a tungsten filament and the filament 111h may be heated by applying current to electrically conductive wires 111f connected to the filament 111h. However, according to an exemplary embodiment, the cathode 111e is not limited to the filament 111h and may include carbon nanotubes which can be driven by a high-speed pulse.

The anode 111c may be formed of copper (Cu) and may be coated with a target material 111d, such as, for example, a high-resistance material such as chromium (Cr), iron (Fe), cobalt (Co), nickel (Ni), tungsten (W), and/or molybdenum (Mo), on a surface facing the cathode 111e. If the melting point of the target material 111d is relatively large, a corresponding focal spot size is small.

If a high voltage is applied between the cathode 111e and the anode 111c, thermoelectrons are accelerated to collide with the target material 111d of the anode 111c, thereby generating X-rays. The generated X-rays are radiated to the outside of the X-ray tube 111 through a window 111i which may be formed as a thin film of beryllium (Be).

The target material 111d may be rotated by a rotor 111b. If the target material 111d is rotated, compared to a case that the target material 111d is not rotated, a heat accumulation rate per unit area may increase tenfold or more, and focal spot size may decrease.

The voltage applied between the cathode 111e and the anode 111c of the X-ray tube 111 may be referred to as tube voltage, and the magnitude thereof may be expressed as kilovolts peak (kVp). If the tube voltage increases, the speed of thermoelectrons increases and thus the energy of X-rays (the energy of photons) generated when thermoelectrons collide with the target material 111d increases. The current flowing in the X-ray tube 111 may be referred to as a tube current and may be expressed as an average number of milliamps (mA). If the tube current increases, the dose of X-rays (the number of X-ray photons) increases.

Therefore, since the energy level of X-rays may be controlled by the tube voltage and the intensity or dose of X-rays may be controlled by the tube current and X-ray exposure time, the energy level and intensity of X-rays radiated toward the object 35 may be controlled based on the type or characteristics of the object 35.

The X-ray generator 110 generates X-rays using the above-described X-ray tube 111 and radiates the generated X-rays toward the subject 30, and more particularly, toward the object 35.

If the X-rays are radiated toward the object 35 from the X-ray generator 110, an attenuation coefficient varies based on a material inside the object 35, and the attenuation coefficient and the attenuation coefficient difference vary based on the energy level of the radiated X-rays. Here, the attenuation coefficient refers to a number that describes how quickly the X-rays are attenuated.

First, the attenuation coefficient varies based on a material inside the object 35. FIG. 4 is a graph illustrating correlations between energy and attenuation coefficient which vary based on a material inside the object 35.

Figure 4:
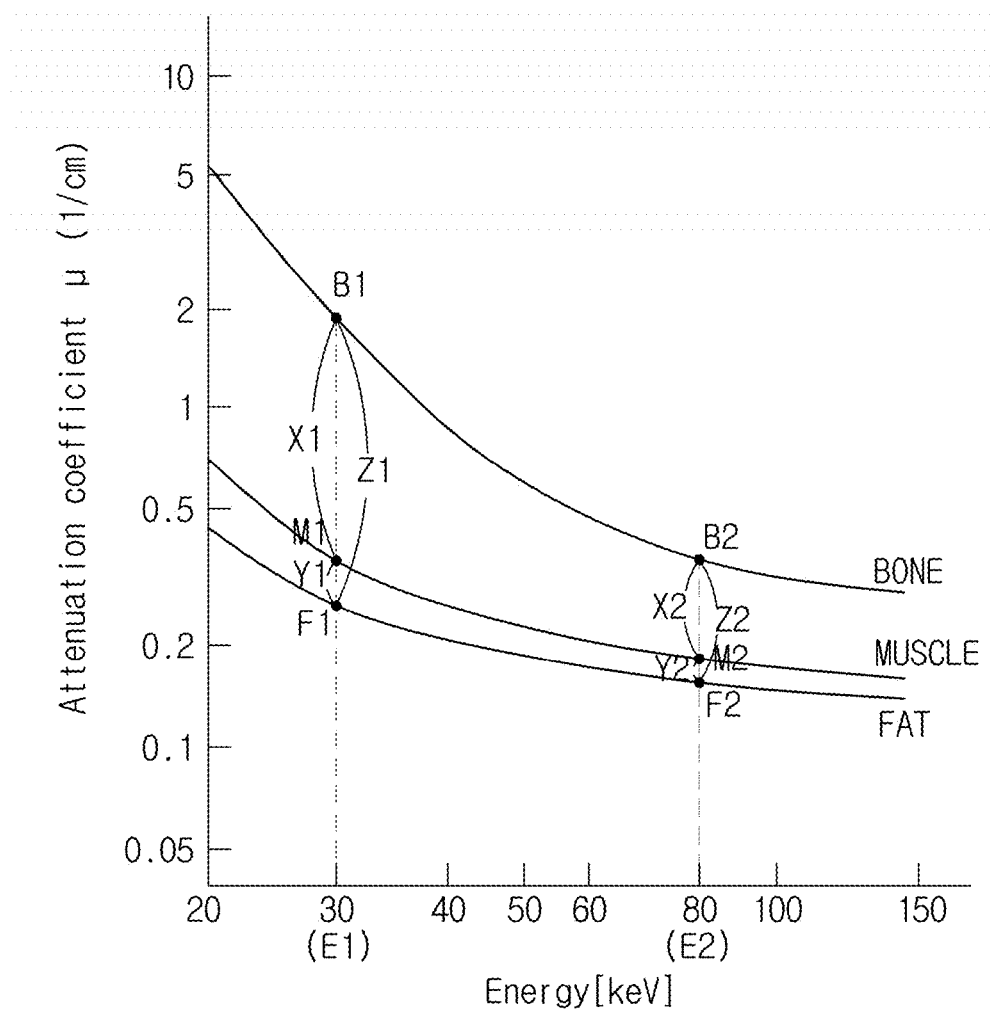
FIG. 4 is a graph illustrating correlations between energy and an attenuation coefficient which vary based on a material inside an object.

Referring to the graph of FIG. 4, a curve indicating an attenuation coefficient of bones is located above a curve indicating an attenuation coefficient of soft tissues (muscles or fat). Specifically, when X-rays having the same energy level, $E_1$, are radiated, an attenuation coefficient $B_1$ of bones is greater than an attenuation coefficient $M_1$ of muscles, and the attenuation coefficient $M_1$ of muscles is greater than an attenuation coefficient $F_1$ of fat.

That is, the different materials inside the object 35 have different attenuation coefficients, and the attenuation coefficient increases based on a hardness of the material.

Second, the attenuation coefficient and the attenuation coefficient difference vary based on the energy level of radiated X-rays.

In the graph of FIG. 4, when X-rays having a relatively low energy level $E_1$ and X-rays having a relatively high energy level $E_2$ are radiated toward bones of the object 35, an attenuation coefficient $B_1$ at the relatively low energy level $E_1$ is greater than an attenuation coefficient $B_2$ at the relatively high energy level $E_2$. Likewise, in the case of muscles or fat, an attenuation coefficient $M_1$ or $F_1$ at the relatively low energy level $E_1$ is greater than an attenuation coefficient $M_2$ or $F_2$ at the relatively high energy level $E_2$.

That is, an attenuation coefficient is relatively large if the energy level of X-rays radiated to the object 35 is correspondingly low.

Further, the attenuation coefficient difference between materials is relatively large if the energy level of X-rays radiated to the object 35 is correspondingly low.

For example, as illustrated in the graph of FIG. 4, an attenuation coefficient difference $X_1$ between bones and muscles (i.e., $B_1-M_1$) when the energy level of the X-ray is $E_1$ is greater than an attenuation coefficient difference $X_2$ between bones and muscles (i.e., $B_2-M_2$) when the energy level of the X-ray is $E_2$. In addition, attenuation coefficient differences $Z_1$ and $Z_2$ between bones and fat (i.e., $B_1-F_1$ and $B_2-F_2$) also have the same result. Although not large, an attenuation coefficient difference $Y_1$ between muscles and fat (i.e., $M_1-F_1$) at the low energy level $E_1$ is greater than an attenuation coefficient difference $Y_2$ between muscles and fat (i.e., $M_2-F_2$) at the high energy level $E_2$.

Such an attenuation coefficient may be expressed as Equation 1 below.

$$I=I_0 \cdot e^{-\mu(E) \cdot T} \quad \text{[Equation 1]}$$

Here, $I_0$ is the intensity of X-rays radiated to a material, I is the intensity of the X-rays which propagate through the material, $\mu(E)$ is an attenuation coefficient of the material with respect to the X-rays having energy E, and T is the thickness of the material through which the X-rays propagate.

According to Equation 1, if the attenuation coefficient increases (that is, if the material is hard or the energy level of radiated X-rays is low) and if the thickness of the material is large, the intensity of the X-rays which propagate through the material decreases.

In short, the attenuation coefficient difference between different materials inside the object 35 varies based on the energy level of X-rays radiated toward the object 35, and thus the X-ray transmittance difference between the materials also varies.

Using the above-described fact that the X-ray transmittance difference between materials inside the object 35 varies based on the energy level of X-rays radiated toward the object 35, an X-ray image in which a contrast between the materials of the object 35 is improved may be obtained. Specifically, X-ray images respectively corresponding to different energy levels may be obtained, and then an ultimate X-ray image in which materials of the object 35 are clearly distinguished or a certain material is shown more vividly than other materials may be generated by using the obtained X-ray images.

Figure 5:
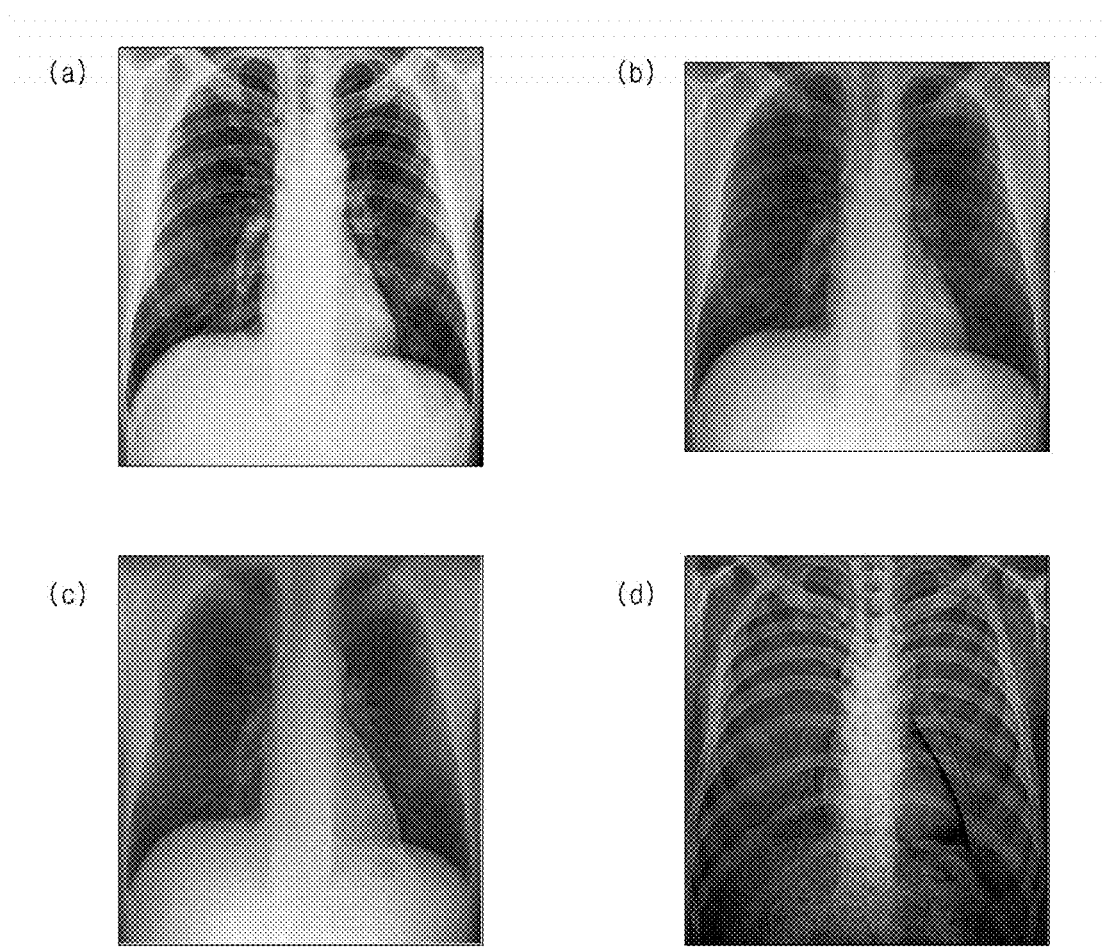
FIG. 5 is a view illustrating a process of obtaining a high-contrast X-ray image.

FIG. 5 is a view illustrating a process of obtaining a high-contrast X-ray image.

Specifically, when the object 35 is the chest, (a) of FIG. 5 illustrates an image of the object 35 generated by radiating low-energy X-rays, (b) of FIG. 5 illustrates an image of the object 35 generated by radiating high-energy X-rays, (c) of FIG. 5 illustrates an image of separated soft tissues of the object 35, and (d) of FIG. 5 illustrates an image of separated bones of the object 35.

Here, the low-energy X-rays refer to X-rays having a low energy level and the high-energy X-rays refer to X-rays having a high energy level. The concepts of the low-energy and high-energy X-rays are relative and are variable depending on the type and/or characteristics of the object 35. For example, if the object 35 is the breast, the low-energy X-rays may have an energy level of 30 keV and the high-energy X-rays may have an energy level of 70 keV. As another example, if the object 35 is the chest, the low-energy X-rays may have an energy level of 70 keV and the high-energy X-rays may have an energy level of 140 keV.

The materials of the object 35 are not separated in the images (a) and (b) of FIG. 5. However, the brightness difference between bones and soft tissues varies between the images of (a) and (b) of FIG. 5. This is because, as described above, the X-ray transmittance difference between the materials varies based on the energy level of X-rays radiated toward the object 35. Using this fact, if dual-energy X-ray absorptiometry is applied, X-ray images of separate materials of the object 35 may be obtained which are similar to the images (c) and (d) of FIG. 5.

That is, if materials to be separated are bones and soft tissues, by multiplying the image of (a) of FIG. 5 by a certain weight and then subtracting it from the image of (b) of FIG. 5, an image which does not show bones but does vividly show soft tissues may be obtained as illustrated in (c) of FIG. 5. Conversely, by multiplying the image of (b) of FIG. 5 by a certain weight and then subtracting it from the image of (a) of FIG. 5, an image which does not show soft tissues but does vividly show bones may be obtained as illustrated in (d) of FIG. 5.

For this reason, multi-energy X-rays which are radiated at different energy levels are used. An X-ray imaging apparatus which is capable of achieving an effect of radiating multi-energy X-rays by radiating single-energy X-rays will now be described.

Figure 6:
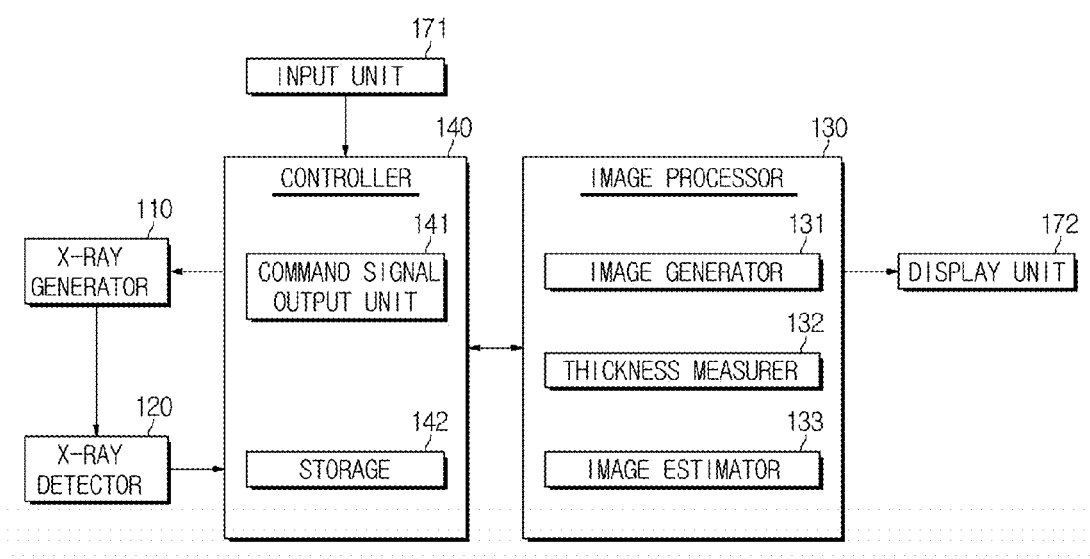
FIG. 6 is a block diagram of an X-ray imaging apparatus according to an exemplary embodiment.

FIG. 6 is a block diagram of an X-ray imaging apparatus 100 according to an exemplary embodiment.

Referring to FIG. 6, the X-ray imaging apparatus 100 may include the X-ray generator 110, the X-ray detector 120, an image processor 130, a controller 140, the input unit 171, and the display unit 172.

The X-ray generator 110 may radiate low-energy X-rays EL or high-energy X-rays EH toward the object 35. That is, single-energy X-rays may be radiated. Here, for convenience of explanation, it is assumed that the low-energy X-rays EL are radiated.

When the low-energy X-rays $E_L$ are radiated toward the object 35, the low-energy X-rays $E_L$ may be repeatedly radiated at a certain time interval. Here, the certain time interval may not be constant. In other words, if second X-rays are radiated toward the object 35 at a time interval $t_1$ after first X-rays are radiated, and third X-rays are radiated at a time interval $t_2$ after the second X-rays are radiated, $t_1$ and $t_2$ may not need to have the same value. The certain time interval and the number of repetitions may be designated by a user via the input unit 171.

If the object 35 is the breast, while the object 35 is being compressed by the compression paddles 103, X-rays may be radiated from above the object 35.

Figure 7:
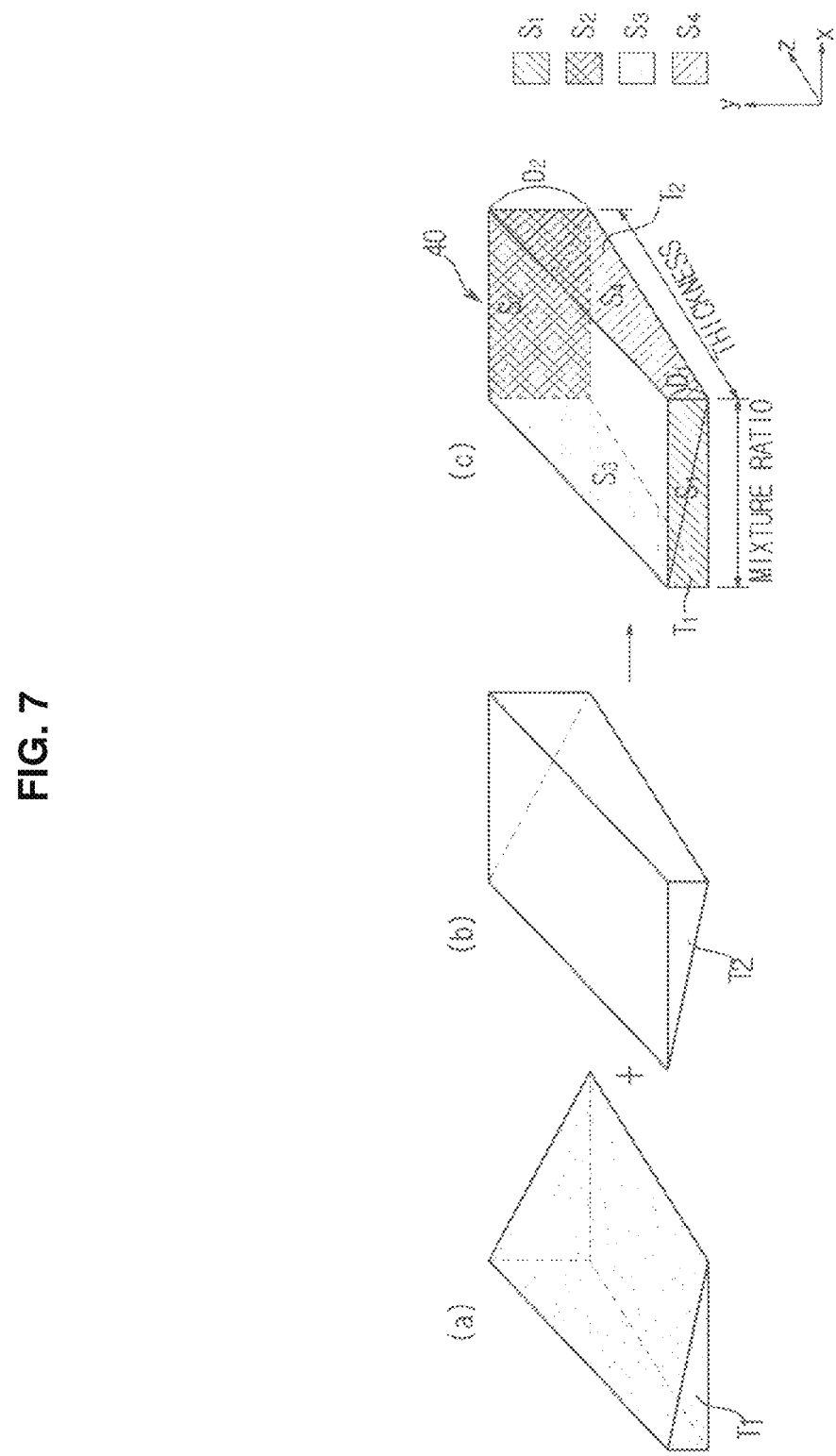
FIG. 7 is a view illustrating a phantom.

The X-ray generator 110 may radiate the low-energy X-rays $E_L$ and the high-energy X-rays $E_H$ toward a phantom 40 (see FIG. 7). That is, dual-energy X-rays may be radiated.

Here, the phantom 40 refers to a model of the object 35 which is formed of the same or similar materials as the materials of the object 35 and is capable of representing the thickness of and a mixture ratio between the materials of the object 35. An example thereof will now be described with reference to FIG. 7.

FIG. 7 is a view illustrating the phantom 40.

If the object 35 is the breast, it may be assumed that the object 35 is formed of two materials such as adipose tissues (i.e., first material $T_1$) and glandular tissues (i.e., second material $T_2$), and has a minimum thickness $D_1$ and a maximum thickness $D_2$ which varies based on location.

With respect to the above-described object 35, by combining the first material $T_1$ illustrated in (a) of FIG. 7 and the second material $T_2$ illustrated in (b) of FIG. 7, the phantom 40 may be generated as illustrated in (c) of FIG. 7.

Specifically, the phantom 40 may be configured to include a rectangular front surface $S_1$ and a rear surface $S_2$ parallel to a plane formed by the x and y axes, and an angled trapezoidal left surface $S_3$ and a right surface $S_4$ parallel to a plane formed by the y and z axes, in such a manner that the thickness in the y direction is equal to $D_1$ on the front surface $S_1$, linearly increases toward the rear surface $S_2$, and is equal to $D_2$ on the rear surface $S_2$.

Here, since the first and second materials $T_1$ and $T_2$ are combined diagonally, a mixture ratio between the first and second materials $T_1$ and $T_2$ may vary from the left surface $S_3$ to the right surface $S_4$ of the phantom 40. That is, the mixture ratio between the first and second materials $T_1$ and $T_2$ in the y direction on the left surface $S_3$ of the phantom 40 may be equal to 1:0. However, since the ratio of the first material $T_1$ linearly decreases while the ratio of the second material $T_2$ linearly increases toward the right surface $S_4$, the mixture ratio between the first and second materials $T_1$ and $T_2$ in the y direction on the right surface $S_4$ may be equal to 0:1.

The phantom 40 formed as described above may be formed of the same materials as the materials of the object 35 and may represent the thickness of and a mixture ratio between the materials of the object 35. However, the phantom 40 is not limited to the above-described configuration and may include any other configuration appropriate as a model of the object 35.

When X-rays are radiated toward the phantom 40, the low-energy X-rays $E_L$ and the high-energy X-rays $E_H$ are separately radiated once each.

The X-ray detector 120 separately detects X-rays which propagate through the object 35 and the phantom 40.

Specifically, since the low-energy X-rays $E_L$ are repeatedly radiated toward the object 35 at the certain time interval, the X-ray detector 120 correspondingly detects X-rays a plurality of times. In addition, since the low-energy X-rays $E_L$ and the high-energy X-rays $E_H$ are separately radiated toward the phantom 40 once each, the X-ray detector 120 correspondingly detects X-rays twice.

Here, the type and/or configuration of the X-ray detector 120 is not restrictive.

Referring again to FIG. 6, the image processor 130 may include an image generator 131, a thickness measurer 132, and an image estimator 133.

The image generator 131 may generate an image of the object 35 and an image of the phantom 40 based on the X-rays detected by the X-ray detector 120. Here, the image of the object 35 is referred to as an object image and the image of the phantom 40 is referred to as a phantom image. Specifically, an image of the object 35 generated by radiating the low-energy X-rays $E_L$ may be referred to as a first object image, and an image of the object 35 generated by radiating the high-energy X-rays $E_H$ may be referred to as a second object image. Likewise, an image of the phantom 40 generated by radiating the low-energy X-rays $E_L$ may be referred to as a first phantom image, and an image of the phantom 40 generated by radiating the high-energy X-rays $E_H$ may be referred to as a second phantom image.

Figure 8:
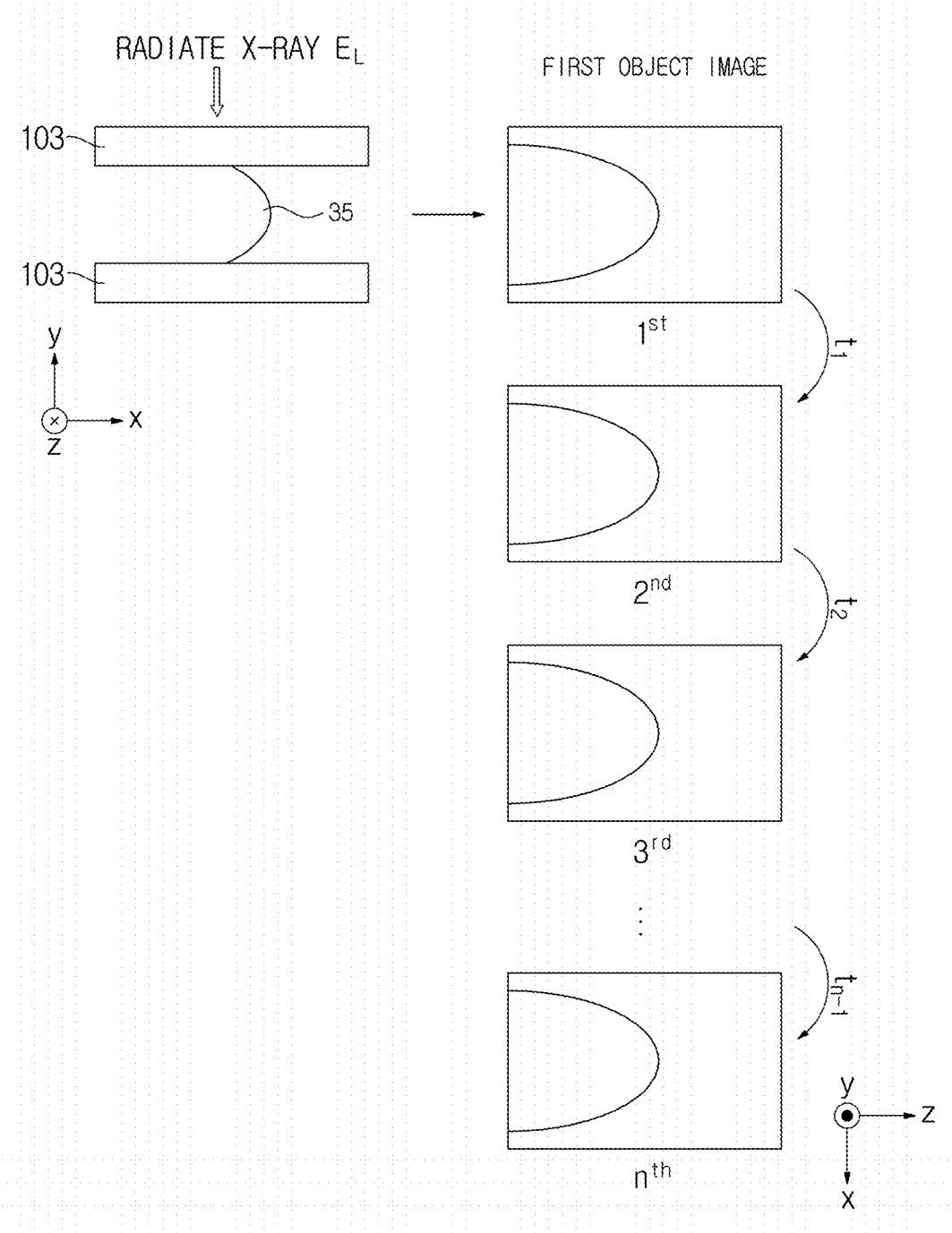
FIG. 8 is a view illustrating a process of generating an object image.
Figure 9:
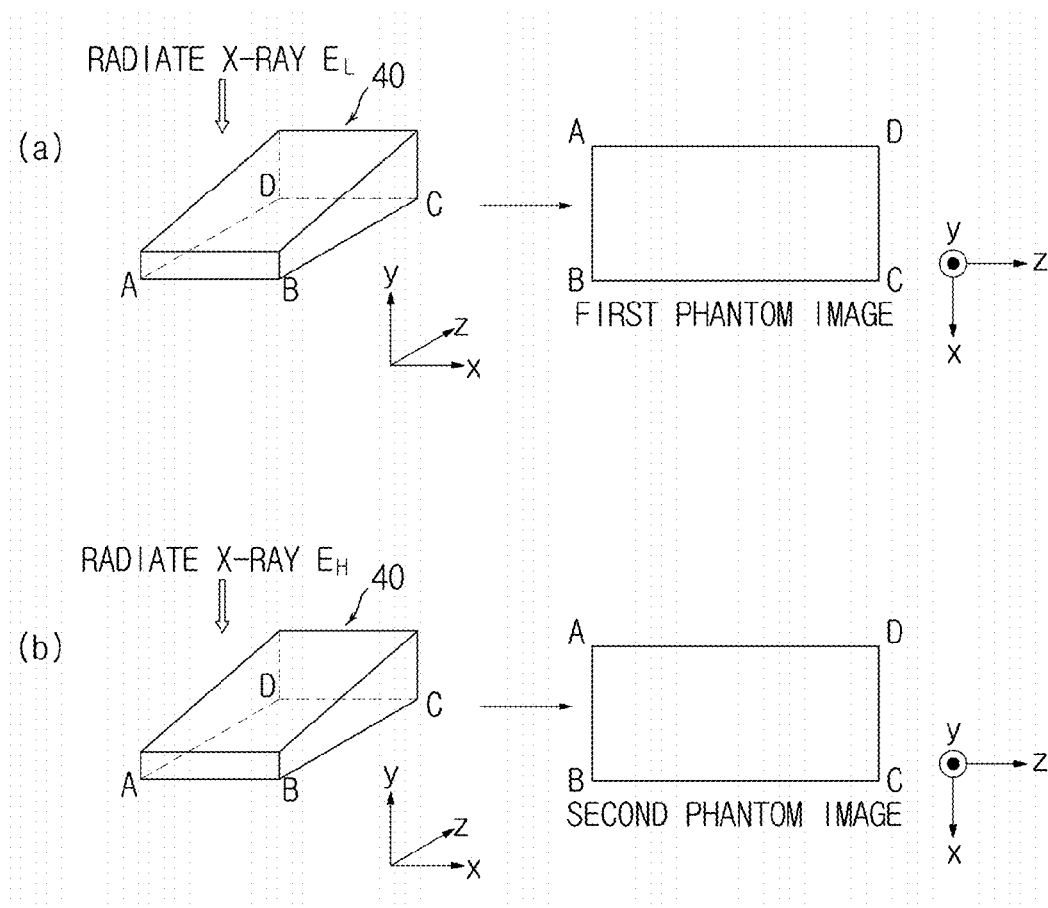
FIG. 9 is a view illustrating a process of generating a phantom image.

FIG. 8 is a view illustrating a process of generating an object image, and FIG. 9 is a view illustrating a process of generating a phantom image.

In FIG. 8, it is assumed that, while the breast, i.e., the object 35, is being compressed by the compression paddles 103, the X-ray generator 110 radiates the low-energy X-rays $E_L$ from above the object 35 n times (assuming that n≥2) at time intervals $t_1, t_2, \ldots, t_{n-1}$ in the y direction, and more particularly, in a direction that the y value decreases, and the X-ray detector 120 detects X-rays which propagate through the object 35 n times.

The image generator 131 generates a $1^{st}$ first object image based on the first detected X-rays, generates a $2^{nd}$ first object image based on the second detected X-rays, and generates a $3^{rd}$ first object image based on the third detected X-rays. In this manner, a total of n first object images corresponding to the number of times that the X-rays are detected are generated.

In this case, the intensities of the detected X-rays correspond to pixel values of the first object images.

In (a) of FIG. 9, it is assumed that the X-ray generator 110 radiates the low-energy X-rays $E_L$ from above the phantom 40 once in a direction that the y value decreases, and the X-ray detector 120 detects X-rays which propagate through the phantom 40.

The image generator 131 generates a rectangular first phantom image based on the detected X-rays. Likewise, the intensity of the detected X-rays corresponds to a pixel value of the first phantom image.

In (b) of FIG. 9, it is assumed that only the energy level of X-rays radiated by the X-ray generator 110 in (a) of FIG. 9 is changed. That is, it is assumed that the X-ray generator 110 radiates the high-energy X-rays $E_H$ from above the phantom 40 once in a direction that the y value decreases, and the X-ray detector 120 detects X-rays which propagate through the phantom 40.

Therefore, the image generator 131 generates a second phantom image having the same form as but a different pixel value from the first phantom image generated in (a) of FIG. 9.

As described above, the image generator 131 may generate a plurality of first object images corresponding to the number of times that X-rays are radiated, and first and second phantom images.

The thickness measurer 132 may measure the thickness of the object 35.

A scheme of measuring the thickness of the object 35 may include, but is not limited to, a scheme using calibration to estimate the thickness of and a mixture ratio between materials of the object 35 from an X-ray image, a scheme using the distance between the compression paddles 130, a scheme using a computed tomography (CT) image, and/or any other suitable scheme.

First, the scheme using calibration will now be described with reference to FIGS. 10 and 11.

Figure 10:
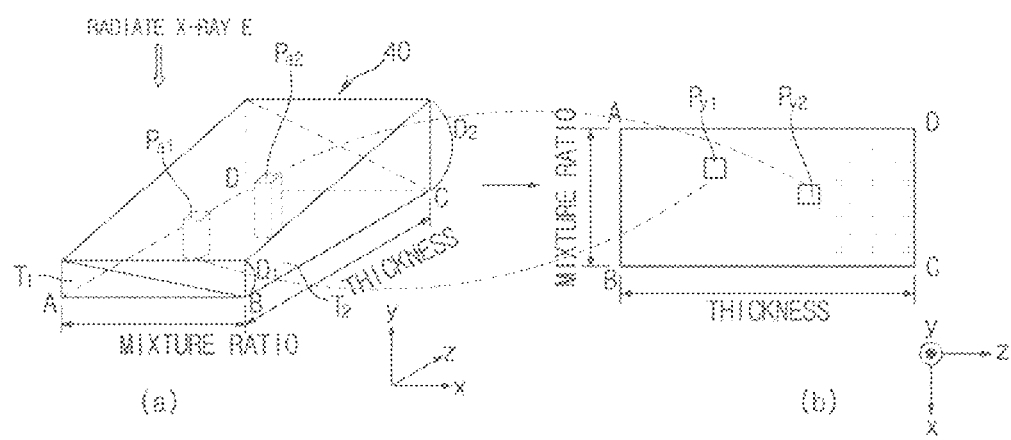
FIG. 10 is a view illustrating correlations between a phantom and a phantom image.
Figure 11:
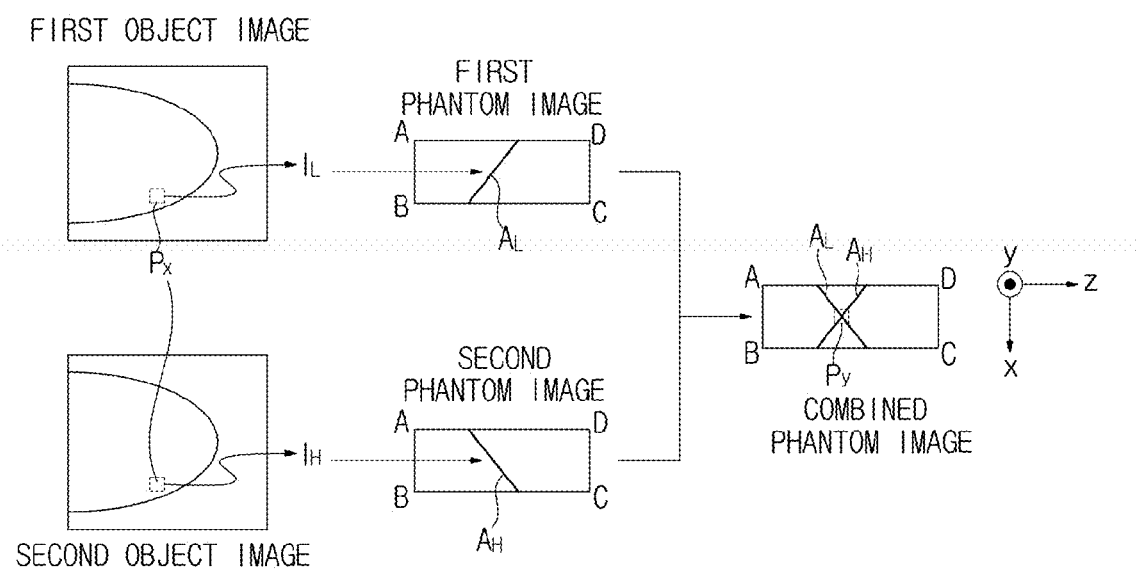
FIG. 11 is a view illustrating a process of performing calibration.

FIG. 10 is a view illustrating correlations between the phantom 40 and a phantom image, and FIG. 11 is a view illustrating a process of performing calibration.

The phantom 40 of (a) of FIG. 10 is the same as that described above in relation to FIG. 7. The phantom image of (b) of FIG. 10 is generated by radiating X-rays from above the phantom 40 as illustrated in FIG. 9, and any of the first and second phantom images may be used. That is, radiated X-rays E may be any of the low-energy X-rays $E_L$ and the high-energy X-rays $E_H$.

Since the phantom image is generated based on X-rays which propagate though the phantom 40, the phantom image includes pixels respectively corresponding to different spots of the phantom 40. Therefore, as illustrated in FIG. 10, a pixel of the phantom image corresponding to part $P_{a1}$ of the phantom 40 may be referred to as $P_{y1}$, and a pixel of the phantom image corresponding to part $P_{a2}$ of the phantom 40 may be referred to as $P_{y2}$.

Then, $P_{y1}$ includes information about the thickness of and a mixture ratio between materials of $P_{a1}$, and $P_{y2}$ includes information about the thickness of and a mixture ratio between materials of $P_{a2}$. For example, in the phantom 40, if $P_{a1}$ has a thickness of 5.5 cm and a mixture ratio of 7:3 between the first and second materials $T_1$ and $T_2$, pixel $P_{y1}$ corresponding to $P_{a1}$ includes information indicating 'the thickness of 5.5 cm and the mixture ratio of 7:3 between the first and second materials $T_1$ and $T_2$. Likewise, in the phantom 40, if $P_{a2}$ has a thickness of 7.5 cm and a mixture ratio of 5:5 between the first and second materials $T_1$ and $T_2$, pixel $P_{y2}$ corresponding to $P_{ae}$ includes information indicating 'the thickness of 7.5 cm and the mixture ratio of 5:5 between the first and second materials $T_1$ and $T_2$. As described above, each pixel of the phantom image includes information about the thickness of and a mixture ratio between materials of a corresponding part of the phantom 40.

Since the phantom 40 is a model of the object 35, the phantom 40 includes parts respectively corresponding to different parts of the object 35.

Consequently, the phantom image includes pixels corresponding to different parts of the object 35, and information about the thickness and a mixture ratio between materials of each pixel is the information of a corresponding part of the object 35.

Therefore, by detecting a respective pixel of the phantom image corresponding to each respective part of the object 35, information about the thickness and a mixture ratio between materials of the part may be achieved. In FIG. 11, calibration is performed using this phenomenon.

Among the plurality of first object images generated by the image generator 131, the $1^{st}$ first object image may be used as a first object image of FIG. 11. In addition, a second object image of FIG. 11 may be generated by radiating the high-energy X-rays $E_H$ using the process that the X-ray generator 110 radiates the low-energy X-rays $E_L$ to generate the $1^{st}$ first object image.

Although the X-ray generator 110 generally radiates single-energy X-rays toward the object 35 as described above, if calibration is used to measure the thickness of the object 35, dual-energy X-rays may be radiated once at an initial stage.

Referring to FIG. 11, pixel values of the same pixel $P_x$ of the first and second object images are calculated. In this case, if the pixel value of pixel $P_x$ of the first object image is referred to as $I_L$ and the pixel value of pixel $P_x$ of the second object image is referred to as $I_H$, $I_L$ and $I_H$ have different values. This is because, as described above, an attenuation coefficient of the same pixel varies based on the energy level of radiated X-rays, and thus the intensity of transmitted X-rays also varies.

Pixels (area $A_L$) having the same pixel value as $I_L$ are indicated on a first phantom image, and pixels (area $A_H$) having the same pixel value as $I_H$ is indicated on a second phantom image. Here, since $I_L$ and $I_H$ have different values, areas $A_L$ and $A_H$ have different slopes.

If the first and second phantom images on which areas $A_L$ and $A_H$ are respectively indicated are aligned and combined, cross point $P_y$ may be detected. That is, pixel $P_y$ of a phantom image (combined phantom image) corresponding to pixel $P_x$ of an object image (first and second object images) is obtained.

As described above in relation to FIG. 10, information about the thickness of (and a mixture ratio between materials of) pixel $P_y$ is the information about the thickness of (and a mixture ratio between materials of) a part of the object 35 corresponding to pixel $P_x$.

If the above-described process is performed on all pixels of the object image (first and second object images), the thickness of (and a mixture ratio between materials of) every part of the object 35 may be estimated.

Second, the scheme using the distance between the compression paddles 130 and the scheme using a CT image will now be described with reference to FIG. 12.

Figure 12:
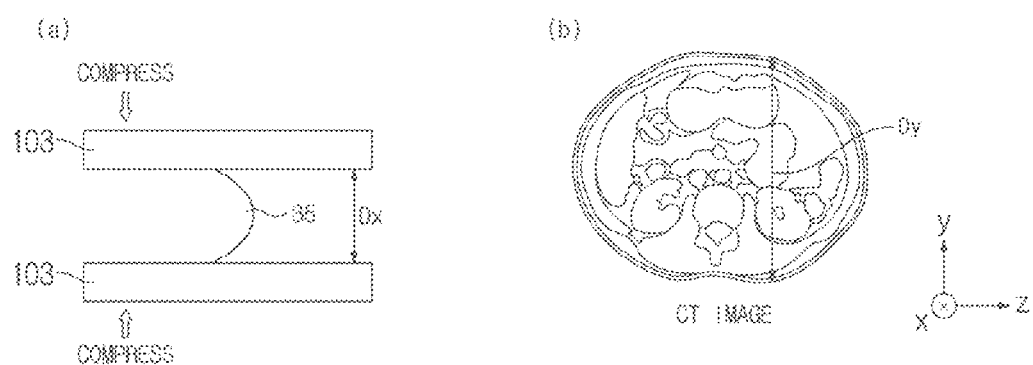
FIG. 12 is a view illustrating a process of measuring the thickness of an object based on the distance between compression paddles or a computed tomography (CT) image.

FIG. 12 is a view illustrating a process of measuring the thickness of the object 35 based on a distance Dx between the compression paddles 130 or a CT image.

As illustrated in (a) of FIG. 12, if the object 35 is the breast, X-rays may be radiated while the object 35 is compressed from above and below using the compression paddles 103 formed as two flat boards. In this case, the distance Dx between the compression paddles 103 may be regarded as being equal to the thickness of the object 35.

A CT apparatus obtains an image of a cross-section of the subject 30 by detecting and reconfiguring X-rays radiated at various angles via 360° rotation, as illustrated in (b) of FIG. 12. In such a CT image, a length Dy in the y direction may be regarded as being equal to the thickness of a corresponding part of the object 35.

The thickness measurer 132 may apply measured thickness information of the object 35 to the first phantom image.

Figure 13:
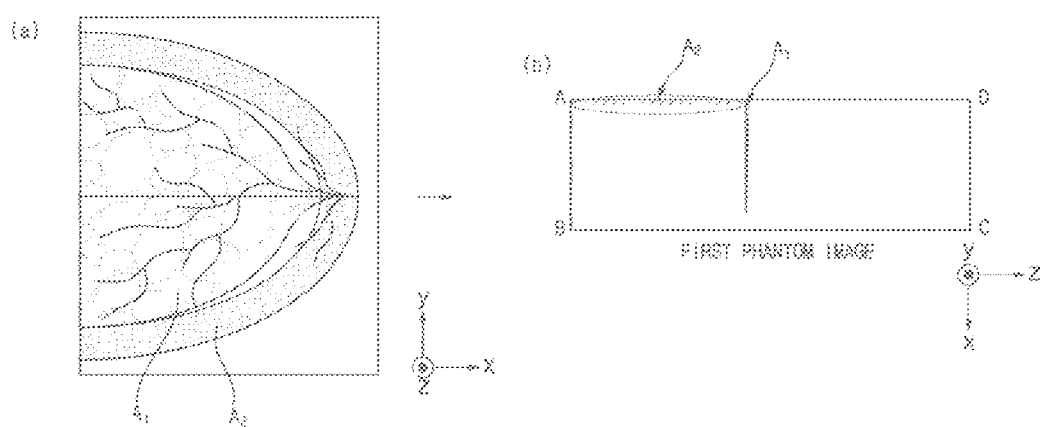
FIG. 13 is a view illustrating a first phantom image to which thickness information of an object is applied.

FIG. 13 is a view illustrating the first phantom image to which the thickness information of the object 35 is applied.

An image of (a) of FIG. 13 is a cross-sectional image of the breast, i.e., the object 35, viewed from above the object 35. Here, area $A_1$ corresponds to an area where a lesion such as a tumor is generated, a region of interest of a user, and a part compressed by the compression paddles 103. Conversely, area $A_2$ corresponds to an edge part which is not compressed by the compression paddles 103.

If the thickness of the above object 35 is measured, the thickness in area $A_1$ is constant and corresponds to the distance between the compression paddles 103 while the thickness in area $A_2$ gradually decreases away from area $A_1$. If a first phantom image of (b) of FIG. 13 is the first phantom image generated in (a) of FIG. 9, only a mixture ratio of materials varies and a thickness is constant in the x direction, but the thickness increases or decreased in the z direction (specifically, the thickness decreases in a direction that the z value decreases).

Therefore, if the thickness information at area $A_1$ and the thickness information at area $A_2$ are applied to the first phantom image, the image illustrated in (b) of FIG. 13 may be obtained.

The image estimator 133 may estimate a second object image inversely using calibration.

Figure 14:
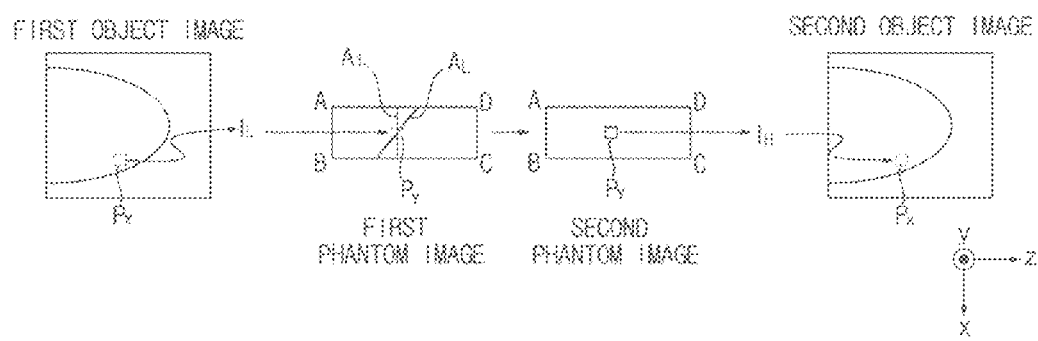
FIG. 14 is a view illustrating a process of estimating a second object image.

FIG. 14 is a view illustrating a process of estimating a second object image.

In FIG. 14, it is assumed that pixel $P_x$ of the first object image has a pixel value of $I_L$. On the first phantom image to which the thickness information (area $A_1$) of the object 35 is applied by the thickness measurer 132, pixels (area $A_L$) having the same pixel value as $I_L$ are detected.

Then, cross point $P_y$ occurs between areas $A_1$ and $A_L$ and a pixel value of $P_y$ is calculated on the second phantom image. If the calculated pixel value is $I_H$, a pixel value of pixel $P_x$ of the second object image is also $I_H$.

If the above-described process is performed on all pixels of the first object image, all pixel values of the second object image may be estimated. Eventually, the second object image may be estimated without radiating the high-energy X-rays $E_H$ toward the object 35.

Although the second object image is estimated based on the first object image in the above exemplary embodiment, the first object image may be estimated based on the second object image.

In addition, an image of the object 35 corresponding to another energy level may also be estimated based on the estimated second object image. For example, if the energy level increases in order of first, second, and third levels, the image estimator 133 may estimate a second object image based on a first object image, and may estimate a third object image based on the estimated second object image. In this case, an $i^{th}$ object image refers to an image of the object 35 generated by radiating $i^{th}$-energy X-rays (i=1, 2, 3). As described above, if the image estimator 133 repeatedly performs an estimation operation, an effect of radiating multi-energy X-rays may be achieved by radiating single-energy X-rays.

In general, the image estimator 133 may estimate n second object images corresponding to n first object images repeatedly generated at a certain time interval. However, if calibration is used to measure the thickness of the object 35, since the image generator 131 already generates both of $1^{st}$ first and second object images, the image estimator 133 may generate n−1 second object images corresponding to n−1 first object images from $2^{nd}$ to $n^{th}$ first object images. As described above, if the image estimator 133 repeatedly performs an estimation operation n (or n−1) times in the time domain, a size variation or process speed of a lesion inside the object 35 may be checked.

Referring again to FIG. 6, the controller 140 may include a command signal output unit (also referred to herein as a "command signal output device") 141 and a storage 142.

If a user inputs a diagnosis command via the input unit 171 connected to the controller 140 via wired or wireless communication, the command signal output unit 141 may output a command signal indicating to radiate X-rays, to the X-ray generator 110.

In this case, the command signal output unit 141 may also output a command signal regarding the energy level of X-rays to be radiated, to the X-ray generator 110. Specifically, a command signal regarding whether to output low-energy X-rays or high-energy X-rays and a command signal regarding the energy value (keV) of X-rays to be radiated may be output. This command signal may be generated according to an energy level input by the user via the input unit 171, or by automatically selecting an energy level based on the type and/or one or more characteristics of the object 35.

In addition, the command signal output unit 141 may also output a command signal regarding a time interval and the number of repetitions in radiating X-rays to the object 35. Likewise, this command signal may be generated according to a time interval and the number of repetitions input by the user via the input unit 171, or by automatically selecting the same based on prestored data.

The command signal output unit 141 may output a command signal indicating to display the first and second object images generated by the image processor 130 on the display unit 172, to the image processor 130.

The storage 142 may store data or algorithms to manipulate the X-ray imaging apparatus 100. For example, the storage 142 may store the energy level of X-rays to be radiated based on the type and/or one or more characteristics of the object 35, a time interval and the number of repetitions in radiating X-rays to the object 35, compressed data of the first and second phantom images and the first and second object images, etc. The storage 142 may also store an algorithm to measure the thickness of the object 35 (in particular, an algorithm to apply calibration), an algorithm to estimate a second object image from a first object image, etc.

The storage 142 may be formed as a non-volatile memory device such as read only memory (ROM), programmable read only memory (PROM), erasable programmable read only memory (EPROM), or flash memory, a volatile memory device such as random access memory (RAM), and/or a storage device such as a hard disk or an optical disc.

However, the storage 142 is not limited thereto and may have other forms known in the art.

Elements of the X-ray imaging apparatus 100 and functions of the elements are described above. A method for controlling the X-ray imaging apparatus 100 will now be described with reference to flowcharts of FIGS. 15 and 16.

Figure 15:
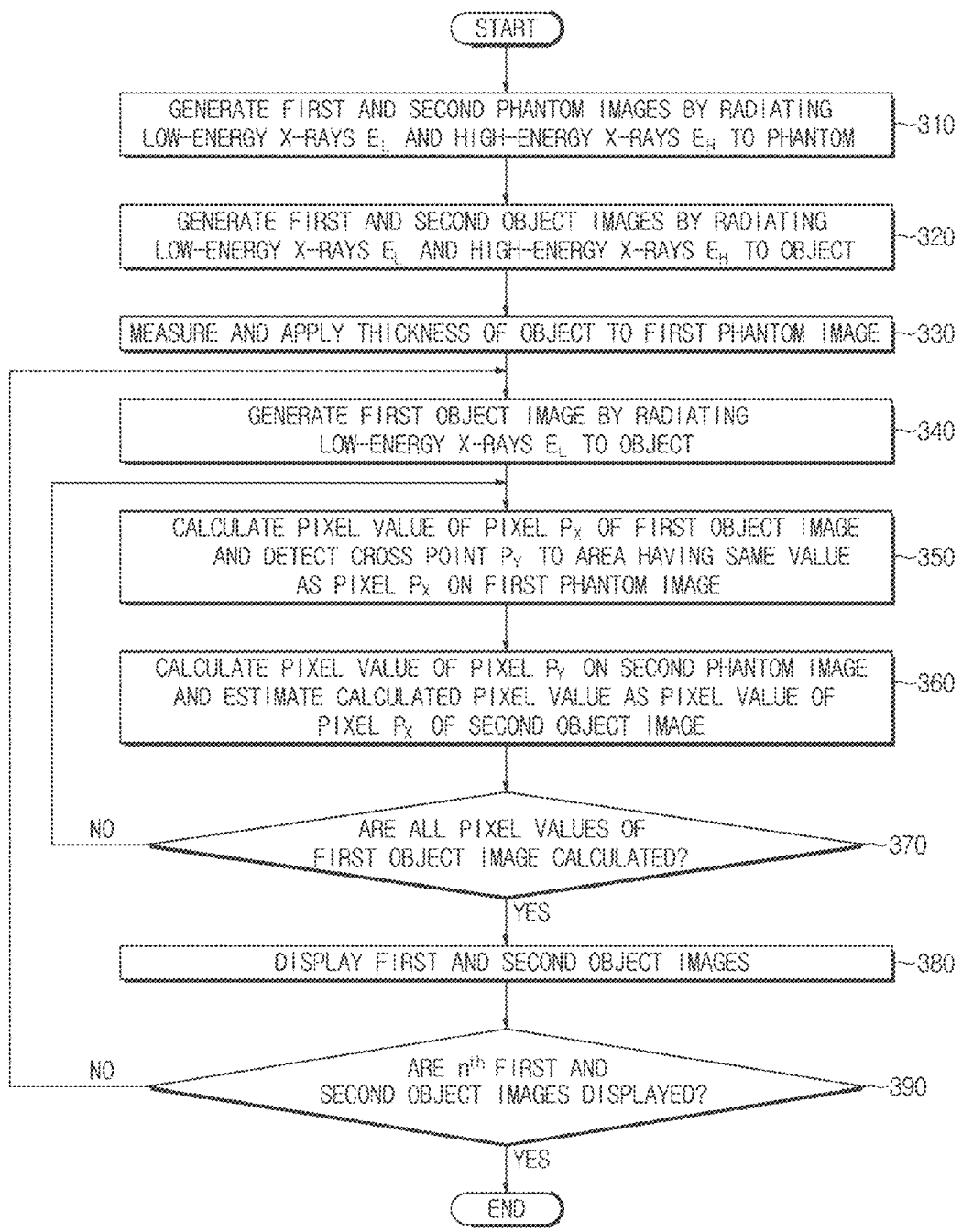
FIG. 15 is a flowchart of a method for controlling an X-ray imaging apparatus, according to an exemplary embodiment.

FIG. 15 is a flowchart of a method for controlling the X-ray imaging apparatus 100, according to an exemplary embodiment.

Referring to FIG. 15, initially, in operation 310, the X-ray generator 110 radiates the low-energy X-rays $E_L$ and the high-energy X-rays $E_H$ toward the phantom 40, and the image generator 131 generates first and second phantom images based on X-rays which propagate through the phantom 40.

In this case, the first phantom image is an image of the phantom 40 generated by radiating the low-energy X-rays $E_L$, and the second phantom image is an image of the phantom 40 generated by radiating the high-energy X-rays $E_H$.

Likewise, in operation 320, the X-ray generator 110 radiates the low-energy X-rays $E_L$ and the high-energy X-rays $E_H$ toward the object 35, and the image generator 131 generates first and second object images based on X-rays which propagate through the object 35.

In this case, the first object image is an image of the object 35 generated by radiating the low-energy X-rays $E_L$, and the second object image is an image of the object 35 generated by radiating the high-energy X-rays $E_H$.

If the object 35 is the breast, it is assumed that, while the object 35 is being compressed by the compression paddles 103, the X-rays are radiated from above the object 35.

In operation 330, thickness information of the object 35 is estimated by performing calibration, and is applied to the first phantom image.

If pixels of an object image are mapped to pixels of a phantom image using pixel values of the generated first and second phantom images and the first and second object images, and if calibration is performed using the fact that the phantom image includes information about the thickness of (and a mixture ratio between materials of) the object 35, the thickness information of the object 35 may be estimated. Calibration has been described in detail above in relation to FIGS. 10 and 11, and thus is not described here.

Then, the estimated thickness information is applied to the first phantom image.

In operation 340, the X-ray generator 110 radiates the low-energy X-rays $E_L$ toward the object 35, and the image generator 131 correspondingly generates the first object image.

When the X-ray generator 110 radiates X-rays toward the object 35, it radiates single-energy X-rays from a second time. The single-energy X-rays may be any of the low-energy X-rays $E_L$ and the high-energy X-rays $E_H$. Here, for convenience of explanation, it is assumed that the low-energy X-rays $E_L$ are radiated.

In operation 350, a pixel value of certain pixel $P_x$ of the first object image is calculated, and a cross point $P_y$ to pixels having the same value as pixel $P_x$ is detected on the first phantom image to which the thickness information of the object 35 is applied.

Here, cross point $P_y$ refers to a cross point between an area of the first phantom image to which the thickness information is applied and an area of the first phantom image in which pixels have the same value as pixel $P_x$.

In operation 360, a pixel value of pixel $P_y$ is calculated on the second phantom image, and is estimated as a pixel value of pixel $P_x$ of the second object image.

In operation 370, a determination is made as to whether all pixel values of the first object image have been calculated.

If all pixel values of the first object image have not been calculated, the method returns to operation 350.

Otherwise, if all pixel values of the first object image have been calculated and thus all pixel values of the second object image are estimated, then in operation 380, the first and second object images are displayed on a screen to be viewed by a user.

In operation 390, a determination is made as to whether $n^{th}$ first and second object images are displayed.

If the $n^{th}$ first and second object images are not displayed, the method returns to operation 340 at a certain time interval.

Otherwise, if the $n^{th}$ first and second object images are displayed, the method terminates.

Here, the certain time interval and the number of repetitions may be determined by the user.

As such, n−1 second object images may be obtained without radiating the high-energy X-rays $E_H$ toward the object 35.

Figure 16:
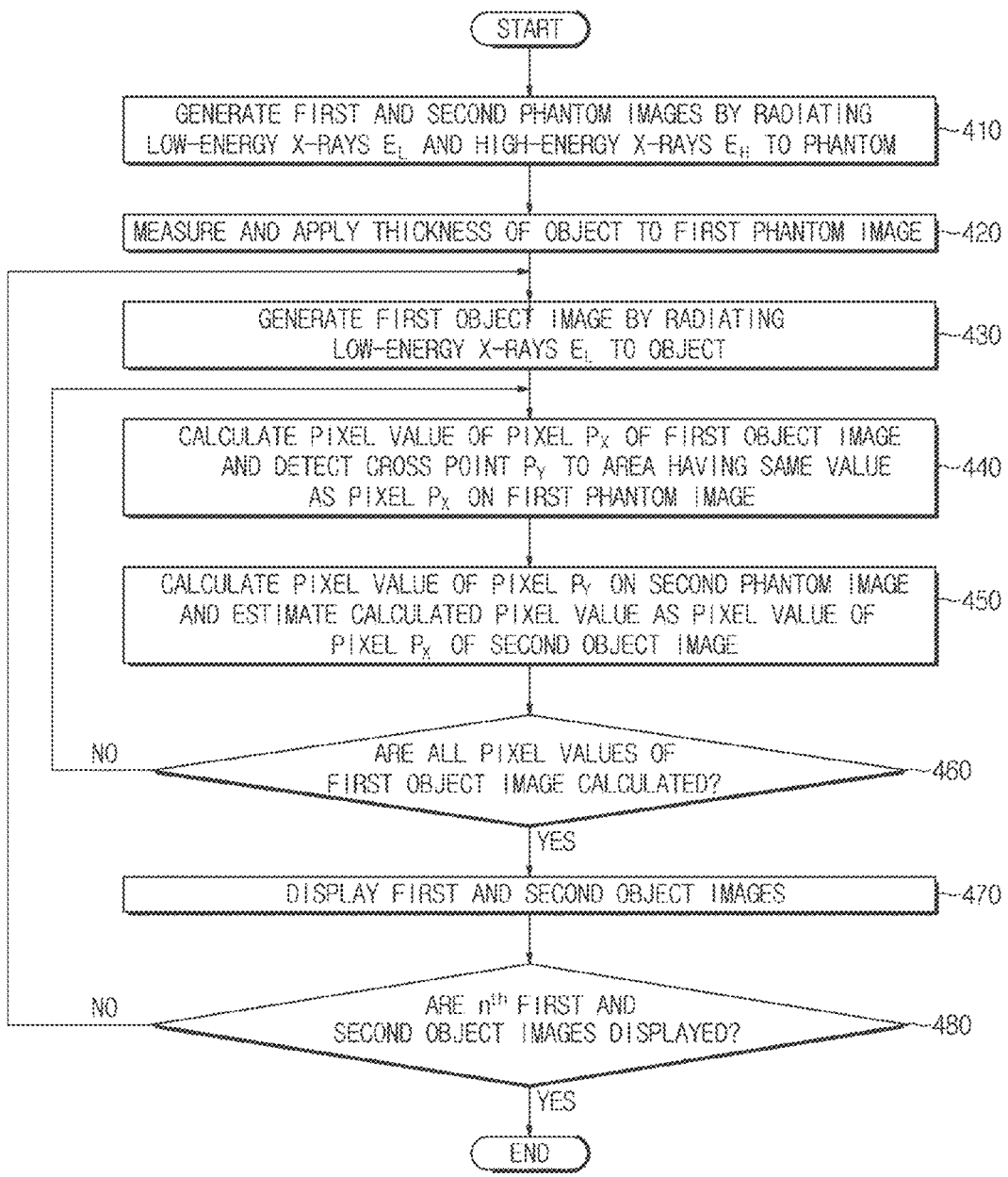
FIG. 16 is a flowchart of a method for controlling an X-ray imaging apparatus, according to another exemplary embodiment.

FIG. 16 is a flowchart of a method for controlling the X-ray imaging apparatus 100, according to another exemplary embodiment.

Referring to FIG. 16, initially, in operation 410, the X-ray generator 110 radiates the low-energy X-rays $E_L$ and the high-energy X-rays $E_H$ toward the phantom 40, and the image generator 131 generates first and second phantom images based on X-rays passing through the phantom 40.

In operation 420, thickness information of the object 35 is measured and applied to the first phantom image.

A scheme of measuring the thickness of the object 35 may include a scheme using the distance between the compression paddles 130, a scheme using a CT image, etc. A detailed description thereof is provided above in relation to FIG. 12, and thus is not provided here.

In operation 430, the X-ray generator 110 radiates the low-energy X-rays $E_L$ toward the object 35, and the image generator 131 correspondingly generates the first object image.

When the X-ray generator 110 radiates X-rays to the object 35, it radiates single-energy X-rays. The single-energy X-rays may be any of the low-energy X-rays $E_L$ and the high-energy X-rays $E_H$. Here, for convenience of explanation, it is assumed that the low-energy X-rays $E_L$ are radiated.

In operation 440, a pixel value of certain pixel $P_x$ of the first object image is calculated, and a cross point $P_y$ to pixels having the same value as pixel $P_x$ is detected on the first phantom image to which the thickness information of the object 35 is applied.

In operation 450, a pixel value of pixel $P_y$ is calculated on the second phantom image, and is estimated as a pixel value of pixel $P_x$ of the second object image.

In operation 460, a determination is made as to whether all pixel values of the first object image have been calculated.

If all pixel values of the first object image have not been calculated, the method returns to operation 440.

Otherwise, if all pixel values of the first object image have been calculated and thus all pixel values of the second object image have been estimated, then in operation 470, the first and second object images are displayed on a screen to be viewed by a user.

In operation 480, a determination is made as to whether $n^{th}$ first and second object images are displayed.

If the $n^{th}$ first and second object images are not displayed, the method returns to operation 430 at a certain time interval.

Otherwise, if the $n^{th}$ first and second object images are displayed, the method terminates.

As such, n second object images may be obtained without radiating the high-energy X-rays $E_H$ toward the object 35.

The above description is provided on the assumption that an image of the object 35 generated by radiating the low-energy X-rays $E_L$ is the first object image, an image of the object 35 generated by radiating the high-energy X-rays $E_H$ is the second object image, an image of the phantom 40 generated by radiating the low-energy X-rays $E_L$ is the first phantom image, an image of the phantom 40 generated by radiating the high-energy X-rays $E_H$ is the second phantom image. However, the first and second object images and the first and second phantom images are not limited thereto provided that the first and second object images are generated by radiating X-rays having different energy levels toward the object 35 and the first and second phantom images are generated by radiating X-rays having different energy levels toward the phantom 40. In this case, the energy levels of the X-rays radiated toward the object 35 and the phantom 40 to generate the first object image and the first phantom image should be the same, and the energy levels of the X-rays radiated toward the object 35 and the phantom 40 to generate the second object image and the second phantom image should also be the same.

As is apparent from the above description, a multi-energy image is estimated using thickness information of an object and a single-energy image, and thus a corresponding exposure time and a corresponding dose of X-rays may be reduced.

In addition, a variation in a lesion inside the object may be checked by repeatedly performing the estimation operation in the time domain.

In this case, any one or more of a variety of schemes may be used to obtain the thickness information of the object.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An X-ray imaging apparatus comprising:
an X-ray generator configured to radiate first-energy X-rays toward an object;
an X-ray detector configured to detect the first-energy X-rays which propagate through the object;
an image processor configured to generate a first object image which corresponds to the detected first-energy X-rays and to estimate a second object image which corresponds to second-energy X-rays based on the generated first object image; and
a controller configured to control the image processor to repeatedly estimate the second object image by controlling the X-ray generator to repeatedly radiate the first-energy X-rays toward the object.

2. The X-ray imaging apparatus according to claim 1, wherein the controller is configured to control the X-ray generator according to a received time interval and a number of repetitions.

3. The X-ray imaging apparatus according to claim 2, wherein the image processor comprises:
an image generator configured to generate the first object image based on the detected first-energy X-rays; and
an image estimator configured to estimate the second object image based on the first object image using thickness information of the object, a first phantom image, and a second phantom image.

4. The X-ray imaging apparatus according to claim 3, wherein the image estimator is further configured to obtain a pixel location of the first phantom image using a pixel value of the first object image and thickness information of the object, to obtain a pixel value of the obtained pixel location on the second phantom image, and to estimate the second object image based on the obtained pixel value.

5. The X-ray imaging apparatus according to claim 4, wherein the image estimator is further configured to obtain the pixel location of the first phantom image as a cross point between an area having the pixel value of the first object image and an area including the thickness information of the object.

6. The X-ray imaging apparatus according to claim 3, wherein the X-ray generator is further configured to radiate the first-energy X-rays and the second-energy X-rays to a phantom, and
wherein the image generator is further configured to generate the first phantom image based on the first-energy X-rays and the second phantom image based on the second-energy X-rays.

7. The X-ray imaging apparatus according to claim 3, wherein the image processor comprises a thickness measurer configured to measure the thickness information of the object.

8. The X-ray imaging apparatus according to claim 7, wherein the thickness measurer is further configured to measure the thickness information of the object according to at least one from among a calibration scheme, a scheme using a distance between compression paddles, and a scheme using a computed tomography (CT) image.

9. The X-ray imaging apparatus according to claim 3, wherein the image processor is further configured to estimate a third object image which corresponds to third energy X-rays based on the estimated second object image.

10. A method for controlling an X-ray imaging apparatus, the method comprising:
an X-ray radiating operation to radiate first-energy X-rays toward an object;
an X-ray detecting operation to detect the first-energy X-rays which propagate through the object;
an image processing operation to generate a first object image which corresponds to the detected first-energy X-rays and to estimate a second object image which corresponds to second-energy X-rays based on the generated first object image; and
a controlling operation to control the second object image to be repeatedly estimated by repeatedly radiating the first-energy X-rays toward the object.

11. The method according to claim 10, wherein the controlling operation comprises controlling the first-energy X-rays to be repeatedly radiated according to a received time interval and a number of repetitions.

12. The method according to claim 11, wherein the image processing operation comprises:

an image generating operation to generate the first object image based on the detected first-energy X-rays; and an image estimating operation to estimate the second object image based on the first object image using thickness information of the object, a first phantom image, and a second phantom image.

13. The method according to claim 12, wherein the image estimating operation comprises:

obtaining a pixel location of the first phantom image using a pixel value of the first object image and thickness information of the object;

obtaining a pixel value of the obtained pixel location on the second phantom image; and estimating the second object image based on the obtained pixel value.

14. The method according to claim 13, wherein, in the image estimating operation, the pixel location of the first phantom image is obtained as a cross point between an area having the pixel value of the first object image and an area including the thickness information of the object.

15. The method according to claim 12, wherein the X-ray radiating operation comprises radiating the first-energy X-rays and the second-energy X-rays toward a phantom, and wherein the image processing operation comprises generating the first phantom image based on the first-energy X-rays and the second phantom image based on the second-energy X-rays.

16. The method according to claim 12, wherein the image processing operation comprises a thickness measuring operation to measure the thickness information of the object.

17. The method according to claim 16, wherein the thickness measuring operation comprises measuring the thickness information of the object according to at least one from among a calibration scheme, a scheme using a distance between compression paddles, and a scheme using a computed tomography (CT) image.

18. The method according to claim 12, wherein the image processing operation comprises estimating a third object image which corresponds to third energy X-rays based on the estimated second object image.

* * * * *